United States Patent [19]

Onodera et al.

[11] Patent Number: 5,750,379
[45] Date of Patent: May 12, 1998

[54] PROCESS FOR THE PRODUCTION OF CARTHAMIN

[75] Inventors: Junichi Onodera; Shingo Sato, both of Yonezawa; Toshio Kashiwagi; Isobe Tetsuhiro, both of Tokyo, all of Japan

[73] Assignee: Toyo Ink Manufacturing Co., Ltd., Tokyo, Japan

[21] Appl. No.: 711,741

[22] Filed: Sep. 10, 1996

[30] Foreign Application Priority Data

| Mar. 18, 1989 | [JP] | Japan | 8-060482 |
| Sep. 11, 1995 | [JP] | Japan | 7-232422 |
| Mar. 18, 1996 | [JP] | Japan | 8-060483 |

[51] Int. Cl.$^6$ .......................... C12P 19/00; A61K 35/78
[52] U.S. Cl. .......................... 435/72; 424/195.1
[58] Field of Search ............... 435/72; 424/195.1

[56] References Cited

PUBLICATIONS

Saito. Z. Naturforsch, vol. 47c, pp. 205–208, 1992.
Saito et al. J. Plant Physiol. vol. 142, pp. 257–264, 1993—Abstract.
Saito. Biochem. Physiol. Pflanzen. vol. 188, pp. 405–417, 1993.
Saito. Plant Sci. vol. 90, pp. 1–9, 1993.
Kumazawa et al. Chemistry Letters, vol. 8, pp. 625–626, 1995.
Saito et al. J. Plant Physiol. vol. 140, pp. 121–123, 1992—Abstract.
Hirota et al., JP49026328, 1974—Abstract.
Wada et al. JP61199798, 1985—Abstract.

*Primary Examiner*—Leon B. Lankford, Jr.
*Assistant Examiner*—Christopher R. Tate
*Attorney, Agent, or Firm*—Wenderoth, Lind & Ponack

[57] ABSTRACT

Carthamin (safflower red dyestuff) which is highly useful but has been limited in use due to its high price, can be efficiently obtained from safflower yellow B dyestuff of which the content in safflower petals is large, and the safflower red dyestuff therefore can be stably provided at a low price.

18 Claims, No Drawings

PROCESS FOR THE PRODUCTION OF CARTHAMIN

BACKGROUND OF THE INVENTION

1. Field of the Invention

The present invention relates to a process for the production of carthamin, which comprises reacting a safflower-yellow B dyestuff with an oxido-reductase and an aldehyde, or with an oxido-reductase which generates hydrogen peroxide together with oxygen as a receptor and an oxido-reductase for which hydrogen peroxide works as a receptor. The carthamin produced by the above process is used as a dyestuff for foods or in cosmetics and pharmaceutical compositions.

2. Description of Related Art

Safflower (*Carthamus tinctorius L.*) is a composite plant and has thistle-shaped clear yellow flowers in the middle of July. Its petals are gathered, dried or mashed and fermented to show a clear red color, and this fermented product has been called "Koka" (safflower) and is highly valued as traditional Chinese medicine or a high-class dye. However, the amount of water-soluble dyestuff (composed of safflower yellow A, safflower yellow B and safflower yellow C) is overwhelmingly large, as large as about 60% by weight, based on the dyestuffs contained in the pedals, and the content of carthamin which is the useful red dyestuff is as small as 0.4 to 0.6% by weight. In recent years, the red dyestuff of safflower is attracting attention as a dyestuff for foods since it is excellent in heat resistance and color tone as compared with red beet, and studies are therefore being made not only on the method of efficiently extracting it but also on the further expansion of use thereof.

Safflower yellow is water-soluble, and carthamin is sparingly soluble in water. On the basis of this difference, a current practice employs a method in which a red color dyestuff is recovered from a residue remaining after the extraction of the yellow dyestuff with water. Since, however, the content of carthamin itself is very small, highly purified red dyestuff carthamin is expensive, which prevents the further expansion of use thereof.

SUMMARY OF THE INVENTION

It is an object of the present invention to provide a process for efficiently producing a red dystuff, carthamin, from safflower yellow B, whose content is nearly 50% by weight, based on yellow dyestuffs which are contained in a large amount in the petals of safflower.

According to the present invention, there is provided a process for the production of carthamin, which comprises reacting an oxido-reductase and an aldehyde with safflower yellow B.

According to the present invention, there is also provided a process for the production of carthamin, which comprises reacting an oxido-reductase which generates hydrogen peroxide together with oxygen as a receptor and an oxido-reductase for which hydrogen peroxide works as a receptor, with safflower yellow B.

According to the present invention 3, there is further provided a process for the production of carthamin, which comprises reacting a hydrolyzate of safflower yellow B with an aldehyde to obtain a carthamin precursor and then oxidizing the carthamin precursor.

DETAILED DESCRIPTION OF THE INVENTION

The present inventors have made diligent studies to overcome the prior art problems and have found that carthamin, a red dyestuff, can be efficiently obtained by reacting an oxido-reductase with a safflower yellow B dyestuff in the presence of an aldehyde. It has been further found that a safflower yellow B dyestuff is efficiently converted to carthamin in the absence of an aldehyde but with a combination of an oxido-reductase which generates hydrogen peroxide together with oxygen as a receptor and an oxido-reductase for which hydrogen peroxide works as a receptor.

The process of the present invention can be carried out by adding an oxido-reductase and an aldehyde, or adding an oxido-reductase which generates hydrogen peroxide together with oxygen as a receptor and an oxido-reductase for which hydrogen peroxide works as a receptor, to an aqueous solution containing a safflower yellow B dyestuff and maintaining the safflower yellow B dyestuff in a buffer solution or water having a pH of 3 to 11, preferably 4 to 9, at a temperature of approximately 5° to 60° C., preferably 20° to 40° C., for 1 minute to 1 weeks, preferably 1 minute to 24 hours.

For promoting the reaction, improving the reaction efficiency or controlling the hydrogen peroxide concentration, it is preferred to simultaneously add a substrate of the oxido-reductase which generates hydrogen peroxide with oxygen as a receptor. Further, for improving the decomposition rate of a safflower yellow B dyestuff, the efficiency of the oxido-reductase in activity, the formation rate of carthamin and the formation efficiency of carthamin, it is preferred to add an immobilizing adsorbent such as cellulose or xanthone. In some cases, oxygen may be introduced into the reaction mixture for several minutes.

It is assumed that carthamin, a red dyestuff, is obtained through the following reaction scheme, in which a safflower yellow B dyestuff is hydrolyzed into a hydrolyzate, which can form a carthamin precursor, and safflomin A, and the former forms carthamin through the carthamin precursor.

The substance called "safflower yellow B hydrolyzate" in the reaction scheme is not only important as an intermediate for forming carthamin from the safflower yellow B dyestuff but also important as an intermediate for the synthesis of other dyestuff, a cosmetic material or a medicament.

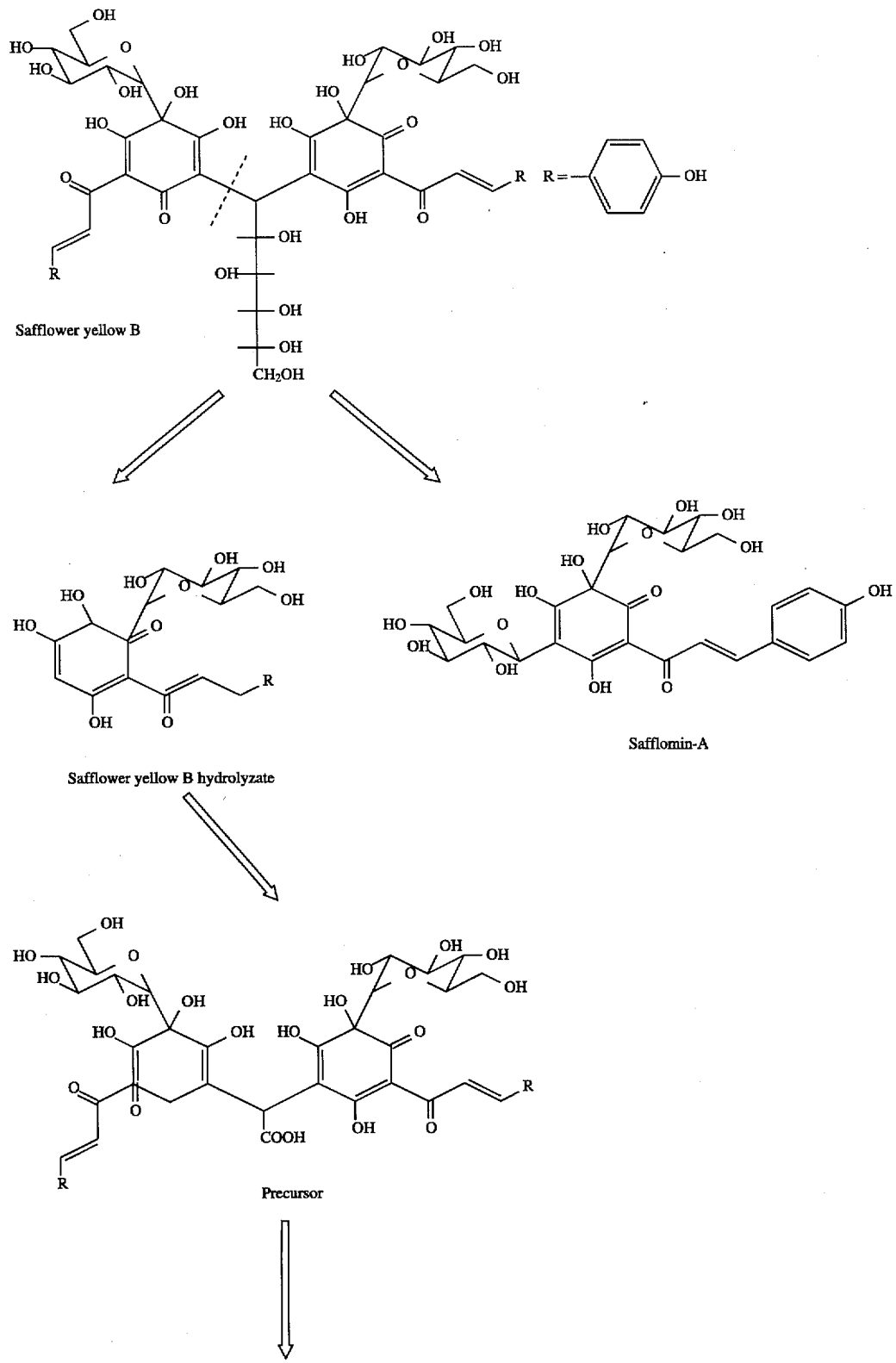

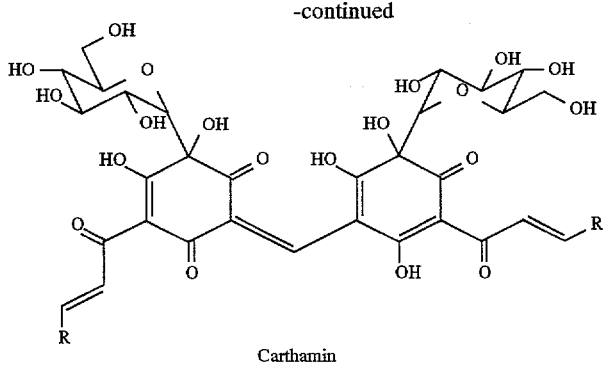
Carthamin

Safflower yellow B is preferably hydrolyzed by the use of an enzyme reaction in the presence of an oxido-reductase, while safflower yellow B may also be hydrolyzed without any enzyme by maintaining it in a buffer solution having a pH of 3 to 11 at a temperature of 5° to 100° C. for 1 hour to 1 week. Further, when the carthamin precursor is converted to carthamin, the reaction proceeds promptly in the presence of an oxido-reductase, while the carthamin precursor may be also converted to carthamin by oxidation with air.

The safflower used in the present invention may be fresh safflower or a dry safflower, and it includes "Mogami Koka", "Chinese Koka", "Okayama No. 1", "Israel" and "California". However, the safflower used in the present invention shall not be limited in kind. The sufflower yellow B dyestuff used in the present invention may have any form such as a purified dyestuff, a crude dyestuff extracted with an alcohol, fresh safflower, dry safflower or crushed petals so long as sufflower yellow B dyestuff is contained therein.

Although depending upon the amount of safflower yellow dystuff (safflower yellow B dyestuff), the amount of the enzyme used in the present invention is 1 unit to 10,000 units based on 1 g of the sufflower yellow dyestuff (sufflower yellow B dyestuff).

The enzyme used in the present invention includes oxidoreductases which are classified as an enzyme for which CH—OH works as a donor, an enzyme which generates hydrogen peroxide with oxygen as a receptor, and an enzyme for which hydrogen peroxide works as a receptor, although the enzyme used in the present invention shall not be limited to the above classification.

The oxido-reductase for which CH—OH works as a donor includes alcohol dehydrogenase, alcohol dehydrogenase (used in combination with NADP+ or NAD+ as a coenzyme), homoserine dehydrogenase, butanediol dehydrogenase, acetone dehydrogenase, glycerol dehydrogenase, propanediol phosphate dehydrogenase, glycerol phosphate dehydrogenase (used in combination with NAD+ as a coenzyme), xylose reductase, arabinitol dehydrogenase, iditol dehydrogenase, galactitol dehydrogenase, mannitol phosphate dehydrogenase, inositol dehydrogenase, glucuronate reductase, glucuronolactone reductase, aldose reductase, glucose dehydrogenase, histidinol dehydrogenase, quinate dehydrogenase, shikimate dehydrogenase, glyoxylate reductase, lactate dehydrogenase, glycerate dehydrogenase, hydroxybutylate dehydrogenase, hydroxyisobutylate dehydrogenase, mevaldate reductase, hydroxymethylglutalyl reductase, hydroxyacyl dehydrogenase, acetoacetyl reductase, maleate dehydrogenase, isocitorate dehydrogenase, phosphogluconate dehydrogenase, gluconate dehydrogenase, arabinosedehydrogenase, glucosedehydrogenase, galactose dehydrogenase, glucose phosphate dehydrogenase, hydroxysteroid dehydrogenase, hydroxycholanate dehydrogenase, allyl alcohol dehydrogenase, lactaldehyde reductase, ribitol dehydrogenase, fructuronate reductase, tagaturonate reductase, hydroxypropionate dehydrogenase, tartronate semialdehyde reductase, hydroxybutylate dehydrogenase, estradiol dehydrogenase, testosterone dehydrogenase, pyridoxine dehydrogenase, hydroxydecanoate dehydrogenase, mannitol dehydrogenase, gluconate dehydrogenase, octanol dehydrogenase, aminopropanol dehydrogenase, butanediol dehydrogenase, lactone aldehyde reductase, lactone aldehyde dehydrogenase, glyoxylate reductase, isopropanol dehydrogenase, hydroxylpyruvate reductase, maleate dehydrogenase, dimethylmaleate dehydrogenase, isopropylmaleate dehydrogenase, ketolate reductoisomerase, hydroxycarboxyadipate dehydrogenase, hydroxymethylglutaryl reductase, acryl alcohol dehydrogenase, oxaloglycolate reductase, tartrate dehydrogenase, glycerol phosphate dehydrogenase, phosphoglycerate dehydrogenase, diodophenylpyruvate reductase, hydroxybenzyl alcohol dehydrogenase, hydroxyfatty acid dehydrogenase, oxoacyl ACP reductase, palmitoyl dihydroxyacetone phosphate reductase, dehydrosphinganine reductase, threonine dehydrogenase, oxoproline reductase, retinol dehydrogenase, pantoate dehydrogenase, pyridoxal dehydrogenase, carnitine dehydrogenase, indole lactate dehydrogenase, imidazole lactate dehydrogenase, indanol dehydrogenase, xylose dehydrogenase, apiose reductase, ribose dehydrogenase, arabinose dehydrogenase, glucose dehydrogenase, galactose dehydrogenase, aldose dehydrogenase, fucose dehydrogenase, sorbose dehydrogenase, fructose dehydrogenase, deoxygluconate dehydrogenase, ketodeoxygluconate dehydrogenase, idonate dehydrogenase, threonate dehydrogenase, ketogluconate dehydrogenase, mannuronate reductase, mannose dehydrogenase, ketorhamnose reductase, deoxytalose dehydrogenase, acetylglucoseamine dehydrogenase, ribitol phosphate dehydrogenase, mannitol dehydrogenase, sorbitol phosphate dehydrogenase, hydroxyprostaglandin dehydrogenase, pinitol dehydrogenase, sequoitol dehydrogenase, perillyl alcohol dehydrogenase, hydroxysteroid dehydrogenase, estradiol dehydrogenase, ethiocholanolone dehydrogenase, sepiapterin reductase, ureidoglycolate dehydrogenase, homoisocitrate dehydrogenase, glycerol dehydrogenase, dihydroxybutylol dehydrogenase, hydroxybutylyl CoA dehydrogenase, acetylenol pyryvoyl glucoseamine reductase, erythrulose reductase, cyclopentanol dehydrogenase, hexadecanol dehydrogenase, hydroxyhexanecarbonate dehydrogenase, hydroxymalonate dehydrogenase, oxopantoyl lactone reductase, oxopantoate reductase, hydroxymethylcholestenoate dehydrogenase, methylenetetrahydroborate reductase, oxoadipate reductase, rhamnose dehydrogenase, cyclohexanediol dehydrogenase, glycolate oxidase, maleate oxidase, glucose oxidase, hexose oxidase, cholestrol oxidase, allyl alcohol oxidase, gulonolactone oxidase, galactose oxidase, pyranose oxidase, sorbose oxidase, pyridoxine oxidase, alcohol oxidase, catechol oxidase, hydroxy acid oxidase, ecdysone oxidase and choline oxidase. However, the oxido-reductase shall not be limited to these.

The oxido-reductase which generates hydrogen peroxide with oxygen as a receptor is generically called "oxidase", and includes glucose oxidase, hexose oxidase, cholesterol oxidase, allyl alcohol oxidase, sorbose oxidase, pyridoxine oxidase, alcohol oxidase, catechol oxidase, hydroxy acid oxidase, ecdysone oxidase, choline oxidase, amino acid oxidase, amine oxidase and uric acid oxidase, although the above oxido-reductase shall not be limited to these. For effectively feeding hydrogen peroxide, a substrate corresponding to the enzyme is desirably present in an amount of not more than 10 mole equivalents, preferably not more than 2 mole equivalents, based on the amount of the safflower yellow B dyestuff, although it may not be present in some cases. The above enzymes may be used alone or in combination.

Glucose oxidase is a typical example of the oxido-reductase which generates hydrogen peroxide with oxygen as a receptor. Glucose oxidase includes those derived from *aspergillus, penicillium amagasakiense* and *penicillium notatum*, although the glucose oxidase shall not be limited to these. Glucose is a corresponding substrate, and glucose is desirably present in an amount of not more than 2 mole equivalents, based on the amount of the safflower yellow B dyestuff, although it may not be present in some cases.

Although not specially limited, the oxido-reductase for which hydrogen peroxide works as a receptor includes NAD+ peroxidase, NADP+ peroxidase, fatty acid peroxidase, cytochrome peroxidase, catalase, peroxidase, iodo peroxidase, glutathione peroxidase and chloride peroxidase.

The above enzymes may be used alone or in combination. The enzyme which requires a coenzyme NAD+ or NADP+ may be used alone. The use of the coenzyme can improve the conversion efficiency.

Catalase and peroxidase are among typical examples of the oxido-reductase for which hydrogen peroxide works as a receptor. Although not specially limited, the catalase includes those purified from a bovine, equine or human liver, the liver of a sheep, a mouse, a pig or a toad, and bacteria such as *Micrococcus lysodeikticus* or *Rhodopseudomonas spheroidus*. Although not specially limited, the peroxidase includes those derived from horseradish, a fig, a radish, a turnip, thyroid, milk, intestine or leukocyte. These enzymes may be used alone or in combination.

The amount of the aldehyde used in the present invention differs depending upon the amount of the safflower yellow B dyestuff. The amount of the aldehyde is ⅕ to 5 g equivalents based on 1 g equivalent of the safflower yellow B dyestuff.

Although not specially limited, the aldehyde used in the present invention includes formaldehyde, acetoaldehyde, butylaldehyde, crotonaldehyde, glyoxal, alkyl ester of glyoxylic acid, glyoxylic acid chloride, glyoxylic acid amide, glyoxylic acid nitrile, aldol, dimethylpropanl, benzaldehyde and its derivative and acrylaldehyde.

The buffer solution used in the present invention has a concentration of 0.001 to 1 mol. Although not specially limited, the buffer solution includes a phosphoric acid buffer solution, a citric acid buffer solution, an acetic acid buffer solution, a tris-hydrochloric acid buffer solution, an ammonium acetate buffer solution, a sodium pyrophosphate buffer solution, a glycine-sodium buffer solution and Good's Buffer.

It is assumed that the process of the present invention proceeds through a conversion scheme in which safflower yellow B is decomposed from the safflower yellow B dyestuff in the presence of an oxido-reductase or under some conditions, an aldehyde acts on the resultant hydrolyzate to form a carthamin precursor, and the formation of carthamin is promoted in the presence of the oxido-reductase or through oxidation. The process of the present invention is also assumed to proceed as follows. The safflower yellow B dyestuff is decomposed into a hydrolyzate which forms the carthamin precursor and a safflomin-A dyestuff under the influence of the oxido-reductase for which the oxygen works as a receptor or some reaction conditions. The hydrolyzate formed at this time forms the carthamin precursor under complex activities of the oxido-reductase for which the oxygen present works as a receptor, a substrate corresponding thereto (glucose if the oxido-reductase is glucose oxidase) and hydrogen peroxide which is consequently formed. Then, the carthamin precursor is converted to carthamin under the complex activities of the hydrogen peroxide and the oxido-reductase for which the hydrogen peroxide works as a receptor.

In both of the above two assumptions, the same result takes place. When the safflower yellow B dyestuff is hydrolyzed in the presence of the enzyme or chemically, a hydrolyzate which forms the carthamin precursor and the safflomin-A dyestuff are formed in equimolar amounts, and the former is converted to carthamin in the presence of the oxido-reductase or under oxidation with air through the carthamin precursor. That is, carthamin in a theoretical amount of 433 mg is obtained from 1 g of safflower yellow B. The actual yield of carthamin is about 90% of the theoretical amount. It has been found that the safflower yellow B dyestuff is efficiently converted to carthamin according to the process of the present invention. The above analyses are easily confirmed by high-performance liquid chromatography.

Carthamin obtained in the present invention is easily recovered by allowing an immobilizing adsorbent to adsorb it. For example, the immobilizing adsorbent includes Duolite S-30, ES-33 and S-37 (supplied by Diamond Shamrock Chemical Co., Ltd.), Amberlite XAD-2, XAD-4, XAD-7 and XAD-8 (supplied by Rohm and Hass), Diaion HP-10, HP-20, HP-21 and HP-40 (supplied by Mitsubishi Chemical Co., Ltd.), KS, HS, AF and L-1 (supplied by Hokuetsu Tanso Kogyo K.K.), and polysaccharides such ascellulose, chitin, chitosan, starch and derivatives of these, although the adsorbent shall not be limited to these.

Further, the co-presence of an immobilizing adsorbent in the reaction system for the conversion from safflower yellow B dyestuff to carthamin not only promotes the formation rate of carthamin but also can increase the yield of carthamin. The amount of the immobilizing adsorbent is preferably 100 mg to 1 kg based on 1 kg of the dry petals of safflower. When purified dyestuff is used, the amount of the adsorbent is calculated relative to the amount of the safflower yellow B dyestuff and carthamin contained in the dry petals.

After the reaction, purified carthamin can be easily obtained through Sephadex which is crosslinked dextran (supplied by Pharmacia) or column chromatography using silica gel, or by a method in which the carthamin is adsorbed on a cellulose powder and fractionated.

The present invention will be explained more in detail hereinafter.

EXAMPLE 1

30 Milligrams of highly purified safflower yellow B dyestuff, 2 mg (25 units) of cholesterol oxidase and 1.5 mg of glyoxylic acid were dissolved in 2 ml of a 0.5M phosphoric acid buffer solution. The mixture was allowed to react for 3 days with stirring under reaction conditions of 25° C. and pH 6.8. The reaction mixture showed a color change from yellow to red. After the reaction, a cellulose powder was added for to stably immobilize and adsorb carthamin as a red dyestuff. Then, the pH of the reaction mixture was adjusted to 5~6 with citric acid to allow the cellulose powder to completely adsorb the carthamin in the reaction mixture. The cellulose powder was recovered by filtration and washed with water to remove water-soluble impurities, and then the carthamin was eluted from the cellulose with methanol. The eluate was fully dried to give a preparation of purified carthamin (yield 3.0 mg).

The analysis results of the infrared absorption spectrum, the ultraviolet absorption spectrum, the mass spectrometry and the thin film chromatography of the above-obtained carthamin completely agreed with those of known carthamin.

EXAMPLE 2

A solution of 1 mg (186 units) of glucose oxidase (derived from *Aspergillus niger*) and 1.5 mg of glyoxylic acid in 2 ml of a 0.5M phosphoric acid buffer solution was added to an aqueous solution of safflower yellow dyestuff (containing 30 mg of safflower yellow B dyestuff) obtained from safflower "Koka" ("California", yellow flower variety) by 70% ethanol extraction. The mixture was allowed to react for 3 days with stirring under reaction conditions of 25° C. and pH 6.8. The reaction mixture showed a color change from yellow to red. After the reaction, a cellulose powder was added to allow the powder to stably immobilize and adsorb the red dyestuff, carthamin. Then, the pH of the reaction mixture was adjusted to 5~6 with citric acid to allow the cellulose powder to completely adsorb the carthamin in the reaction mixture. The cellulose powder was recovered by filtration and washed with water to remove water-soluble impurities, and then the carthamin was eluted from the cellulose with 80% methanol. The eluate was fully dried to give a preparation of purified carthamin (yield 5.0 mg).

The analysis results of the infrared absorption spectrum, the ultraviolet absorption spectrum, the mass spectrometry and the thin film chromatography of the above-obtained carthamin completely agreed with those of known carthamin.

EXAMPLE 3

A solution of 1 mg (186 units) of glucose oxidase (*Aspergillus niger*) and 0.3 mg (30 units) of peroxidase (horseradish) in 2 ml of a 0.5M phosphoric acid buffer solution was added to 30 mg of a highly purified safflower yellow B dyestuff. The mixture was allowed to react for 2 days with stirring under reaction conditions of 25° C. and pH 6.8 to decompose the safflower yellow B dyestuff. Then, 2.0 mg of formaldehyde was added to the reaction mixture, and the mixture was allowed to react for 1 day while it was stirred under reaction conditions of 25° C. and pH 6.8. The reaction mixture showed a color change from yellow to red. After the reaction, a cellulose powder was added to allow the powder to stably immobilize and adsorb the red dyestuff, carthamin. Then, the pH of the reaction mixture was adjusted to 5~6 with citric acid to allow the cellulose powder to completely adsorb the carthamin in the reaction mixture. The cellulose powder was recovered by filtration and washed with water to remove water-soluble impurities, and then the carthamin was eluted from the cellulose with ethanol. The eluate was fully dried to give a preparation of purified carthamin (yield 7.5 mg).

The analysis results of the infrared absorption spectrum, the ultraviolet absorption spectrum, the mass spectrometry and the thin film chromatography of the above-obtained carthamin completely agreed with those of known carthamin.

EXAMPLE 4

A highly purified safflower yellow B dyestuff in an amount of 30 mg was dissolved in 2 ml of a 0.2M acetic acid buffer solution (pH 6.8), and the mixture was allowed to react at 25° C. for 2 days with stirring, to decompose the safflower yellow B. Then, 1.5 mg of glyoxylic acid and 0.3 mg (30 units) of peroxidase (horseradish) were added to the reaction mixture. The mixture was allowed to react for 1 day with stirring under conditions of 25° C. and pH 6.8. The reaction mixture showed a color change from yellow to red. After the reaction, a cellulose powder was added to allow the powder to stably immobilize and adsorb the red dyestuff, carthamin. Then, the pH of the reaction mixture was adjusted to 5~6 with citric acid to allow the cellulose powder to completely adsorb the carthamin in the reaction mixture. The cellulose powder was recovered by filtration and washed with water to remove water-soluble impurities, and then the carthamin was eluted from the cellulose with 70%ethanol. The eluate was fully dried to give a preparation of purified carthamin (yield 4.5 mg).

The analysis results of the infrared absorption spectrum, the ultraviolet absorption spectrum, the mass spectrometry and the thin film chromatography of the above-obtained carthamin completely agreed with those of known carthamin.

EXAMPLE 5

Highly purified safflower yellow B dyestuff (30 mg), 5 mg of glucose, 1 mg (186 units) of glucose oxidase (*Aspergillus niger*), 1.5 mg of glyoxylic acid and 0.3 mg (30 units) of peroxidase (horseradish) were dissolved in 2 ml of a 0.5M phosphoric acid buffer solution. The mixture was allowed to react for 3 days with stirring under conditions of 25° C. and pH 6.8. The reaction mixture showed a color change from yellow to red. After the reaction, a cellulose powder was added to allow the powder to stably immobilize and adsorb the red dyestuff, carthamin. Then, the pH of the reaction mixture was adjusted to 5~6 with citric acid to allow the cellulose powder to completely adsorb the carthamin in the reaction mixture. The cellulose powder was recovered by filtration and washed with water to remove water-soluble impurities, and then the carthamin was eluted from the cellulose with ethanol. The eluate was fully dried to give a preparation of purified carthamin. The yield of the carthamin was 12.3 mg, or 94.6% of the theoretical value (13 mg).

The analysis results of the infrared absorption spectrum, the ultraviolet absorption spectrum, the mass spectrometry and the thin film chromatography of the above-obtained carthamin completely agreed with those of known carthamin.

EXAMPLE 6

Highly purified safflower yellow B dyestuff (30 mg), 1 mg (250 units) of alcohol dehydrogenase (Gluconobacter), 0.5 mM NAD+, 1.5 mg of glyoxylic acid and 0.3 mg (30 units) of peroxidase (horseradish) were dissolved in 2 ml of a 60 mM sodium pyrophosphate buffer solution. The mixture was allowed to react for 2 days with stirring under conditions of 25° C. and pH 8.5. The reaction mixture showed a color change from yellow to red. After the reaction, a cellulose powder was added to allow the powder to stably immobilize and adsorb the red dyestuff, carthamin. Then, the pH of the reaction mixture was adjusted to 5~6 with citric acid to allow the cellulose powder to completely adsorb the carthamin in the reaction mixture. The cellulose powder was recovered by filtration and washed with water to remove water-soluble impurities, and then the carthamin was eluted from the cellulose with methanol. The eluate was fully dried to give a preparation of purified carthamin. The yield of the carthamin was 11.3 mg, or 86.9% of the theoretical value (13 mg).

The analysis results of the infrared absorption spectrum, the ultraviolet absorption spectrum, the mass spectrometry and the thin film chromatography of the above-obtained carthamin completely agreed with those of known carthamin.

EXAMPLE 7

1 gram (18,600 units) of glucose oxidase (*Aspergillus niger*), 1 g of glyoxylic acid and 300 mg (30,000 unit) of peroxidase (horseradish) were dissolved in 2 liters of a 0.5M acetic acid buffer solution, and 100 g of dry safflower (Chinese Koka) was added. The mixture was allowed to react for 3 hours with stirring under conditions of 25° C. and pH 6.8. The reaction mixture showed a color change from yellow to red. After the reaction, a cellulose powder was added to allow the powder to stably immobilize and adsorb the red dyestuff, carthamin. Then, the pH of the reaction mixture was adjusted to 5~6 with citric acid to allow the cellulose powder to completely adsorb the carthamin in the reaction mixture. The cellulose powder was recovered by filtration and washed with water to remove water-soluble impurities, and then the carthamin was eluted from the cellulose with methanol. The eluate was fully dried to give a purified preparation of carthamin. The yield of the carthamin obtained by adding the oxido-reductase was 178 mg. The analysis results of the infrared absorption spectrum, the ultraviolet absorption spectrum, the mass spectrometry and the thin film chromatography of the above-obtained preparation of purified carthamin completely agreed with those of known carthamin.

EXAMPLE 8

A safflower yellow dyestuff (30 mg) obtained from fresh "Mogami Koka" (safflower) by methanol extraction, 1 mg (186 units) of glucose oxidase (*Aspergillus niger*), 1.5 mg of glyoxylic acid and 0.3 mg (30 units) of peroxidase (horseradish) were dissolved in 2 ml of a 0.5M trishydrochloric acid buffer solution. The mixture was allowed to react for 3 days with stirring under conditions of 25° C. and pH 6.8. The reaction mixture showed a color change from yellow to red. After the reaction, the pH of the reaction mixture was adjusted to 5~6 with citric acid to precipitate carthamin in the reaction mixture, and the carthamin was recovered by centrifugal separation, washed with 0.5% citric acid and dried to give a preparation of purified carthamin. The yield of the carthamin was 2.4 mg. The analysis results of the infrared absorption spectrum, the ultraviolet absorption spectrum, the mass spectrometry and the thin film chromatography of the above-obtained preparation of purified carthamin completely agreed with those of known carthamin.

EXAMPLE 9

Glucose-oxidase-producing bacteria *Aspergillus niger* was implanted in 100 ml of an agar-free potato dextrose medium together with 3 g of a safflower yellow dyestuff obtained from dry Chinese "Koka" by ethanol extraction and 10 g of a cellulose powder, and cultured for 3 days at 25° C. at a pH of 5~6 with shaking the medium. The culture showed a color change from yellow to red. After the culturing, the cellulose powder adsorbing carthamin was recovered by filtration, washed with water to remove water-soluble impurities and made weakly alkaline with a sodium carbonate solution to elute the red dyestuff carthamin from the cellulose. The pH of the eluate was adjusted to 5~6 with citric acid to precipitate the carthamin, and the carthamin was recovered by filtration, purified and dried to give a preparation of purified carthamin. The yield of the carthamin was 240 mg.

The analysis results of the infrared absorption spectrum, the ultraviolet absorption spectrum, the mass spectrometry and the thin film chromatography of the above-obtained preparation of purified carthamin completely agreed with those of known carthamin.

EXAMPLE 10

A highly purified safflower yellow B dyestuff (100 mg), 50 mg of glucose, 50 units of glucose oxidase and 100 units of peroxidase were dissolved in 2 ml of a 0.5M citric acid buffer solution, and 50 mg of a cellulose powder was added for allowing the powder to stably immobilize and adsorb carthamin to be formed. The mixture was allowed to react for 15 minutes under reaction conditions of 25° C. and pH 5.7. The reaction mixture showed a color change from yellow to red. After the reaction, the cellulose powder was recovered by filtration and washed with water to remove water-soluble impurities, and then the carthamin was eluted from the cellulose with methanol. The eluate was fully dried to give a purified preparation of carthamin. The yield of the was 41.8 mg.

The analysis results of the infrared absorption spectrum, the ultraviolet absorption spectrum, the mass spectrometry and the thin film chromatography of the above-obtained preparation of purified carthamin completely agreed with those of known carthamin.

EXAMPLE 11

1.5 Grams of a safflower yellow dyestuff crude powder (containing about 100 mg of safflower yellow B dyestuff) obtained from fresh safflower "Koka" (California (yellow flower variety) by 70% ethanol extraction, 100 mg of glucose, 25 units of glucose oxidase and 200 units of peroxidase were dissolved in 10 ml of a 0.5M phosphoric acid buffer solution, and 100 mg of a cellulose powder was added for allowing the powder to stably immobilize and adsorb carthamin to be formed. The mixture was allowed to react for 1 hour with stirring under reaction conditions of 25° C. and pH 6.8. The reaction mixture showed a color change from yellow to red. After the reaction, the pH of the reaction mixture was adjusted to 5~6 with citric acid to allow the cellulose powder to completely adsorb the carthamin in the reaction mixture. The cellulose powder was recovered by filtration and washed with water to remove water-soluble impurities, and then the carthamin was eluted from the cellulose with 80% methanol. The eluate was fully dried to give a preparation of purified carthamin. The yield of the carthamin was 41.3 mg.

The analysis results of the infrared absorption spectrum, the ultraviolet absorption spectrum, the mass spectrometry and the thin film chromatography of the above-obtained preparation of purified carthamin completely agreed with those of known carthamin.

EXAMPLE 12

A highly purified safflower yellow B dyestuff (100 mg), 50 units of glucose oxidase and 100 units of peroxidase were dissolved in 2 ml of a 0.5M citric acid buffer solution, and 50 mg of a cellulose powder was added for allowing the powder to stably immobilize and adsorb carthamin to be formed. The mixture was allowed to react for 24 hours under reaction conditions of 25° C. and pH 5.7. The reaction mixture showed a color change from yellow to red. After the reaction, the cellulose powder was recovered by filtration and washed with water to remove water-soluble impurities, and then the carthamin was eluted from the cellulose with methanol. The eluate was fully dried to give a preparation of purified carthamin. The yield of the carthamin was 28.8 mg.

The analysis results of the infrared absorption spectrum, the ultraviolet absorption spectrum, the mass spectrometry and the thin film chromatography of the above-obtained preparation of purified carthamin completely agreed with those of known carthamin.

EXAMPLE 13

5 Grams of dry petals of safflower "Koka" from Shin-Chan, China, 500 mg of glucose, 75 units of glucose oxidase and 1,500 units of peroxidase were dissolved in 100 ml of a 0.5M citric acid buffer solution, and 2 g of a cellulose powder was added for allowing the powder to stably immobilize and adsorb carthamin to be formed. The mixture was allowed to react for 18 hours with shaking under reaction conditions of 25° C. and pH 5.7. The reaction mixture showed a color change from yellow to red. After the reaction, the cellulose powder was recovered by filtration and washed with water to remove water-soluble impurities, and then the carthamin was eluted from the cellulose with dimethylformamide. The eluate (150 g) was diluted to 200 ml with dimethylformamide, and measured for absorption intensity at 530 nm. Separately, the above procedures were repeated without glucose, glucose oxidase and peroxidase, and the resultant eluate was measured for absorption intensity at 530 nm. The yield of the carthamin obtained by adding glucose, glucose oxidase and peroxidase was about 2.5 times as large as the yield of the carthamin obtained without adding glucose, glucose oxidase and peroxidase.

EXAMPLE 14

5 Grams of dry petals of safflower "Koka" from Un-nan, China, 500 mg of glucose, 75 units of glucose oxidase and 1,500 units of peroxidase were dissolved in 100 ml of a 0.5M citric acid buffer solution, and 2 g of a cellulose powder was added for allowing the powder to stably immobilize and adsorb carthamin to be formed. The mixture was allowed to react for 18 hours with shaking under reaction conditions of 25° C. and pH 5.7. The reaction mixture showed a color change from yellow to red. After the reaction, the cellulose powder was recovered by filtration and washed with water to remove water-soluble impurities, and then the carthamin was eluted from the cellulose with dimethylformamide. The eluate (150 g) was diluted to 200 ml with dimethylformamide, and measured for absorption intensity at 530 nm. Separately, the above procedures were repeated without glucose, glucose oxidase and peroxidase, and the resultant eluate was measured for absorption intensity at 530 nm. The yield of the carthamin obtained by adding glucose, glucose oxidase and peroxidase was about 7 times as large as the yield of the carthamin obtained without adding glucose, glucose oxidase and peroxidase.

EXAMPLE 15

5 Grams of fresh petals of safflower "Mogami Koka" from preferably Yamagata, Japan, 500 mg of glucose, 75 units of glucose oxidase and 1,500 units of peroxidase were dissolved in 100 ml of a 0.5M citric acid buffer solution, and 2 g of a cellulose powder was added for allowing the powder to stably immobilize and adsorb carthamin to be formed. The mixture was allowed to react for 18 hours with shaking under reaction conditions of 25° C. and pH 5.7. The reaction mixture showed a color change from yellow to red. After the reaction, the cellulose powder was recovered by filtration and washed with water to remove water-soluble impurities, and then the carthamin was eluted from the cellulose with dimethylformamide. The eluate (150 g) was diluted to 200 ml with dimethylformamide, and measured for absorption intensity at 530 nm. Separately, the above procedures were repeated without glucose, glucose oxidase and peroxidase, and the resultant eluate was measured for absorption intensity at 530 nm. The yield of the carthamin obtained by adding glucose, glucose oxidase and peroxidase was about 10 times as large as the yield of the carthamin obtained without adding glucose, glucose oxidase and peroxidase.

According to the present invention, the safflower red dyestuff (carthamin) which has high usefulness but has been limited in use due to its high price can be efficiently obtained from safflower yellow B dyestuff of which the content in safflower petals is large, and the safflower red dyestuff therefore can be stably provided at a low price.

What is claimed is:

1. A process for the production of carthamin, which comprises reacting an aqueous solution of a safflower yellow B dyestuff with an oxido-reductase and an aldehyde other than saccharide for a suitable time and under suitable conditions to obtain a carthamin, the reaction proceeding through the formation of a hydrolyzate of the safflower yellow B dyestuff, and then isolating the carthamin with an immobilizing adsorbent.

2. A process according to claim 1, wherein the aqueous solution of a safflower yellow B dyestuff is an aqueous solution of an extract prepared by extracting safflower petals.

3. A process according to claim 1, wherein the oxido-reductase is added to the aqueous solution of a safflower yellow B dyestuff to hydrolyze the safflower yellow B dyestuff and the aldehyde other than saccharide is added to a resultant hydrolyzate.

4. A process according to claim 1, wherein the oxido-reductase and the aldehyde other than saccharide are added to a hydrolyzate of safflower yellow B dyestuff.

5. A process according to claim 1, wherein the aldehyde other than saccharide is selected from acetaldehyde, glyoxylic acid or an alkyl ester of glyoxylic acid.

6. A process according to claim 1, wherein the oxido-reductase is at least one member selected from the group consisting of an enzyme for which CH—OH works as a donor, an enzyme which generates hydrogen peroxide with oxygen as a receptor and an enzyme for which hydrogen peroxide works as a receptor.

7. A process according to claim 1, wherein the oxido-reductase which generates hydrogen peroxide with oxygen as a receptor is an oxido-reductase for which saccharides are substrates.

8. A process according to claim 7, wherein saccharide is further added.

9. A process according to claim 1, wherein the oxido-reductase is a combination of an alcohol dehydrogenase with nicotinamide-adenine dinucleotide (NAD+) or nicotinamide-adenine dinucleotide phosphate (NADP+) as a coenzyme thereof.

10. A process for the production of carthamin, which comprises reacting an oxido-reductase which generates hydrogen peroxide with oxygen as a receptor and an oxido-reductase for which hydrogen peroxide works as a receptor with an aqueous solution of a safflower yellow B dyestuff for a suitable time and under suitable conditions to obtain a carthamin through a hydrolyzate of the safflower yellow B dyestuff, and then isolating the carthamin with an immobilizing adsorbent.

11. A process according to claim 10, wherein the aqueous solution of a safflower yellow B dyestuff is an aqueous solution of an extract prepared by extracting safflower petals.

12. A process according to claim 10, wherein the oxido-reductase which generates hydrogen peroxide with oxygen as a receptor is an oxido-reductase for which saccharides are substrates.

13. A process according to claim 12, wherein saccharide is further added.

14. A process according to claim 10, wherein the oxido-reductase for which hydrogen peroxide works as a receptor is peroxidase.

15. A process according to claim 10, wherein the oxido-reductase which generates hydrogen peroxide with oxygen as a receptor is glucose oxidase.

16. A process according to claim 15, wherein glucose is further added.

17. A process for the production of carthamin, which comprises reacting a hydrolyzate of a safflower yellow B dyestuff with an aldehyde other than saccharide for a suitable time and under suitable conditions to obtain a carthamin, and then isolating the carthamin with an immobilizing adsorbent.

18. A process according to claim 17, wherein the aldehyde other than saccharide is selected from acetaldehyde, glyoxylic acid or an alkyl ester of glyoxylic acid.

* * * * *

UNITED STATES PATENT AND TRADEMARK OFFICE
CERTIFICATE OF CORRECTION

PATENT NO. : 5,750,379
DATED : May 12, 1998
INVENTOR(S) : Onodera et al.

It is certified that error appears in the above-identified patent and that said Letters Patent is hereby corrected as shown below:

In columns 3 and 4 of the above-identified patent, the chemical formula, designated as "Safflower yellow B hydrolyzate" should be corrected to read as follows:

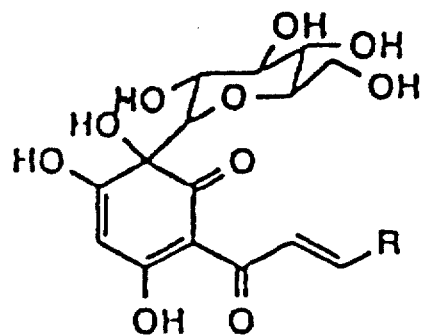

Safflower yellow B hydrolyzate

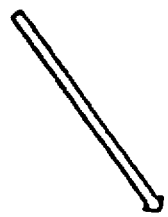

In columns 3 and 4 of the above-identified patent, the chemical formula, designated as "Precursor" should be corrected to read as follows:

UNITED STATES PATENT AND TRADEMARK OFFICE
CERTIFICATE OF CORRECTION

PATENT NO. : 5,750,379
DATED : May 12, 1998
INVENTOR(S) : Onodera et al.

It is certified that error appears in the above-identified patent and that said Letters Patent is hereby corrected as shown below:

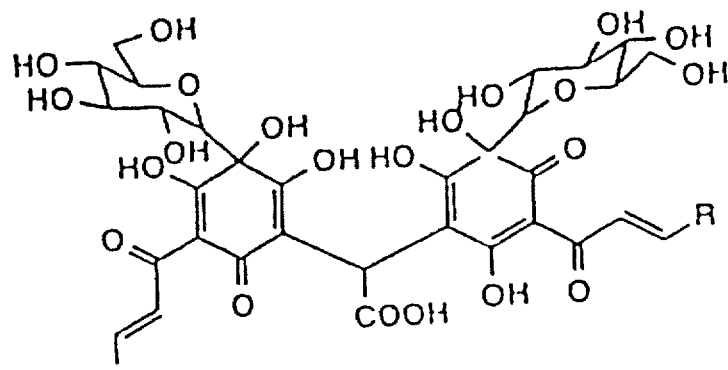

Precursor

Signed and Sealed this

Fourth Day of May, 1999

Attest:

Q. TODD DICKINSON

Attesting Officer

Acting Commissioner of Patents and Trademarks